United States Patent
Triplett et al.

(10) Patent No.: US 6,889,003 B2
(45) Date of Patent: *May 3, 2005

(54) METHOD AND APPARATUS FOR POSITIONING A WICK MATERIAL IN A VAPOR-DISPENSING DEVICE

(75) Inventors: Carl Triplett, Scottsdale, AZ (US); Mengtao Pete He, Scottsdale, AZ (US); Christopher J. Wolpert, Scottsdale, AZ (US); Kristopher J. Stathakis, Scottsdale, AZ (US); Debra Park, Mesa, AZ (US)

(73) Assignee: The Dial Corporation, Scottsdale, AZ (US)

(*) Notice: Subject to any disclaimer, the term of this patent is extended or adjusted under 35 U.S.C. 154(b) by 107 days.

This patent is subject to a terminal disclaimer.

(21) Appl. No.: 10/666,635

(22) Filed: Sep. 18, 2003

(65) Prior Publication Data

US 2004/0062531 A1 Apr. 1, 2004

Related U.S. Application Data

(63) Continuation of application No. 10/095,788, filed on Mar. 11, 2002, now Pat. No. 6,697,571.

(51) Int. Cl.[7] ................................................. F24F 6/08
(52) U.S. Cl. ........................................ 392/390; 392/395
(58) Field of Search ................................. 219/386, 390, 219/393, 394, 395; 122/366; 261/94, 97, 99

(56) References Cited

U.S. PATENT DOCUMENTS 6,697,571 B2 * 2/2004 Triplett et al. .............. 392/395

* cited by examiner

Primary Examiner—Sang Paik
(74) Attorney, Agent, or Firm—Snell & Wilmer L.L.P.

(57) ABSTRACT

The present invention achieves advancement in the art by providing a method and apparatus for selective positioning of a wick material in a vapor-dispensing device that facilitates effective fragrance vapor delivery while offering significant advantages in manufacture, assembly, product performance, and product safety. In one embodiment, the wick is suitably selected and positioned such that sufficient surface area of the wick material is suitably exposed to the heating unit to enable effective evaporation of a vaporizable liquid, but the wick height relative to the heating element minimizes the amount of surface area of the wick in proximity to the heating element. Additionally, the positioning can reduce the need for protective overcaps and other apparatus for protecting the wick.

9 Claims, 3 Drawing Sheets

METHOD AND APPARATUS FOR POSITIONING A WICK MATERIAL IN A VAPOR-DISPENSING DEVICE

CROSS-REFERENCE TO RELATED APPLICATION

This application is a continuation of U.S. patent application Ser. No. 10/095,788 entitled "Method And Apparatus For Positioning A Wick Material In A Vapor-Dispensing Device," filed Mar. 11, 2002, now U.S. Pat. No. 6,697,571, and is incorporated herein by reference.

FIELD OF INVENTION

This invention generally relates to vapor-dispensing devices, and more particularly, to a method and apparatus for positioning a wick material in a vapor-dispensing device.

BACKGROUND OF THE INVENTION

There have been various methods devised to attempt to regulate the diffusion of volatile materials especially with regard to the vapor delivery of fragrances and/or deodorizers. Exemplary prior art devices which relate to this are U.S. Pat. Nos. 525,646; 1,123,036; 1,129,897; 1,323,659; 1,377,909; 2,383,960; 2,507,889; 2,616,759; 2,657,090; 2,787,496; 2,797,844; 2,878,060; 2,961,167; 2,975,464; 3,104,816; 3,239,145; 3,550,853; 3,633,881; 3,679,133; 3,804,331; 4,014,501; 4,094,639; 4,413,779; 4,663,315; 4,739,928; 5,038,394; 5,647,053; 5,903,710; 5,945,094; 5,976,503; and 6,104,867. The primary function of these types of devices has generally been the counteracting of malodors through the delivery of aesthetically pleasing fragrance vapors, or facilitating the delivery of other vapors, such as insecticides or other compositions.

In general, vapor-dispensing products typically include a fragrance-reservoir and a transport system from which fragrance is evaporated into the surrounding air. For example, in such system the liquid to be evaporated is transported from a reservoir via a wick material partially immersed in the liquid. In such a system, in general, the liquid is transported through the wick by capillary action. Many of these systems, such as the system described in U.S. Pat. No. 6,104,867 ("the '867 patent"), include a housing unit into which the liquid reservoir is placed. The housing of such devices advantageously includes a heating unit.

In such devices, the heating element delivers kinetic energy to molecules of the liquid as contained in the wick, thereby increasing the rate of evaporation to obtain higher fragrance intensity and uniform delivery density over time. Typically, in such units, a plug unit is plugged onto a conventional electrical outlet, thereby causing the heating unit to heat the liquid and vaporized liquid that have been drawn up into the wick. The wick and/or bottle unit containing the wick are suitably configured to such that the wick material is placed, when completely assembled, in proximity to the heating element. For example preferably, in most such devices, care is taken to ensure that the wick material, and particularly the uppermost portion thereof extends at least into, or more preferably into and through the typically circumferentially arranged heating unit.

While devices so configured typically ensure effective vaporization of the liquid to be dispensed, various difficulties can be encountered through use of the devices. For example, as explained in some detail in the '867 patent, one of these difficulties (addressed by the guidance and/or stabilization systems described in the '867 patent) is that the wick may become damaged either during insertion, use and/or removal of the wick containing reservoir (e.g., bottle). For example, during insertion and/or removal of the reservoir (e.g., bottle) the wick may be caused to contact the heating element. Furthermore, movement of the reservoir (e.g., bottle) relative to the housing during use or otherwise may give rise to deleterious or disadvantageous interactions between the wick and, for example, the hearing unit.

Products currently on the market have utilized wicks constructed of compressed graphite, porous ceramic, or fibrous bundles. See, for example, U.S. Pat. No. 4,663,315 issued May 5, 1987 to Hasegawa et al, and U.S. Pat. No. 5,647,053 issued Jul. 8, 1997 to Shroeder et al. In these cases, the transport mechanism is capillary action of liquid passing through the structure of a wick, which in use, is contained within the heating element. Notably, and as discussed in more detail below, with momentary reference to FIGS. 1A and 1B and 2A and 2B, each of these exemplary prior art devices clearly require the wide material to be placed, when in use, well within the heating element, and often, beyond the heating element. (FIGS. 1A and 1B are Figures from the '315 Hasegawa et al patent, while FIGS. 2A and 2B are Figures from the '053 Schroeder et al. patent).

Various methods for connecting the fragrance liquid reservoir to a housing unit of a vapor-dispensing device have been developed and are known. Typically, such methods comprise simple snap-type mechanisms, as shown in the aforementioned '867 patent, or screw-thread designs, such as are shown on the '315 patent to Hasegawa. With such systems, particularly when used in a wick containing vaporizer, the wick may be damaged by being crushed or bent by careless interconnection, or be overheated by contact with the heating element during operation, due to instability and improper positioning of the wick material relative to the heating element. This same instability and improper positioning may cause uneven heating of the wick, result in diminished evaporative performance, and consumer frustration.

In attempts to minimize damage, overheating and instability, overcaps and other means of protecting the wick by covering the and supporting the wick, including the portion protruding through the heating element may be employed. However, instability and improper positioning still may cause uneven heating of the wick, result in diminished evaporative performance, and consumer frustration. Moreover, the overcaps can present additional costs to the units and bottles. Thus, there exists a need for a method for positioning a wick material in a vapor-dispensing device that addresses the disadvantages of the prior art.

SUMMARY OF THE INVENTION

While the way in which the present invention addresses the disadvantages of the prior art will be discussed in greater detail below, in general, the present invention achieves advancement in the art by providing a method and apparatus for selective positioning of a wick material in a vapor-dispensing device that facilitates effective fragrance vapor delivery while offering significant advantages in manufacture, assembly, product performance, and product safety.

For example, in accordance with one embodiment of the present invention through effective alignment and positioning of the wick relative to a heating element in a vapor-dispensing device, effective vaporization of the vaporizable liquid can be obtained without subjecting the wick material to possible damage due to contact with the heating unit of the vaporizer during insertion, removal and/or use. In accordance with one aspect of this embodiment, the wick is suitably selected and positioned such that sufficient surface area of the wick material is suitably exposed to the heating unit to enable effective evaporation of a vaporizable liquid, but the wick height relative to the heating element minimizes the amount of surface area of the wick in proximity to the heating element. Additionally, the positioning can reduce the need for protective overcaps and other apparatus for protecting the wick.

Further benefits and advantages of the various aspects and embodiments of the present invention are described in detail hereinbelow.

BRIEF DESCRIPTION OF THE DRAWINGS

The subject matter of the present invention is particularly pointed out and distinctly claimed in the concluding portion of the specification. A more complete understanding of the present invention, however, may best be obtained by referring to the detailed description and claims in connection with the drawing figures, wherein:

DETAILED DESCRIPTION

The following description is of exemplary embodiment of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth in the appended claims.

Figure 3:
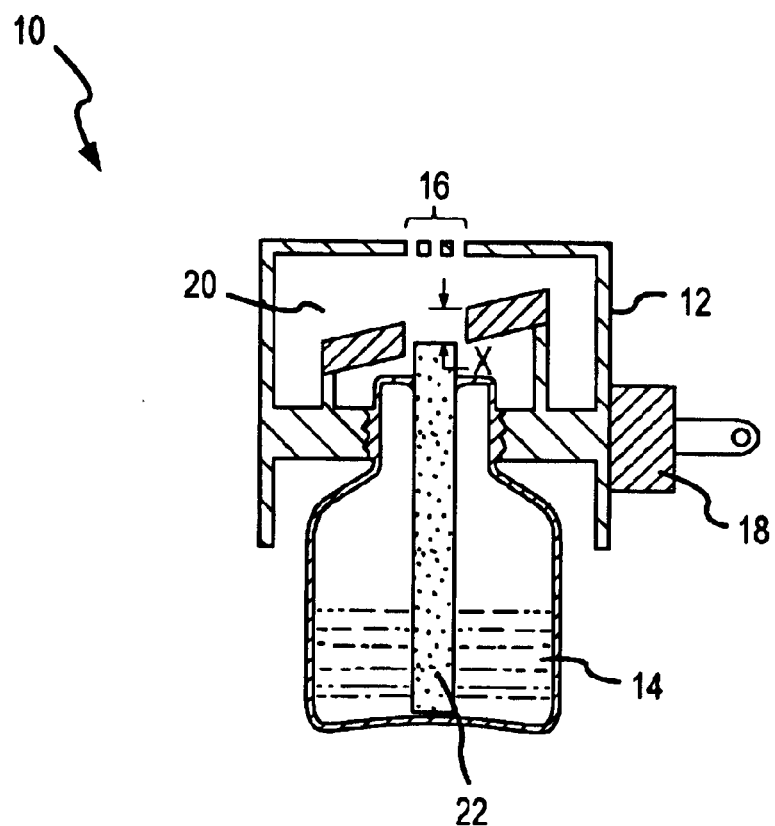
FIG. 3 is a cross-sectional view of an exemplary liquid vaporizer system in accordance with various aspects of the present invention.

In the context of the present invention the method and apparatus hereof find particular use in connection with liquid vaporizer systems. With reference to FIG. 3, an exemplary liquid vaporizer system 10 in accordance with various aspects of one embodiment of the present invention suitably comprises a housing unit 12 and a reservoir (e.g., bottle) unit 14. Reservoir unit 14 is suitably configured for disposition in conjunction with housing 12 and for retention therewithin.

Various methods for connecting the liquid reservoir 14 to a housing unit 12 of a vapor-dispensing system 10 have been developed and are known. Typically, such methods comprise simple snap-type mechanisms or screw-thread designs.

Momentarily, generally speaking, various liquid vaporizers are known and any number of such dispensers are suitable for use in accordance with the present invention. That is, any liquid dispensing device which facilitates the transfer of a liquid through a fluid transfer mechanism (e.g., a wick) which is configured to be heated through use of a heating unit can feasibly incorporate various aspects of the present invention. For example, a typical non-limiting example used herein is an electric liquid vaporizer comprising a housing unit configured to receive a liquid container or bottle portion. In such systems, typically the bottle portion includes some type of a wick or wick system which permits the liquid, which is ultimately to be vaporized, to be absorbed therein through capillary action. The housing unit of such a system generally contains a heating mechanism, typically electrically activated. The bottle portion which generally contains the liquid for vaporization, is usually configured for attachment to the housing such that the wick is suitably positioned proximate the heating mechanism so that the liquid will be vaporized. In general, however, it should be appreciated that any liquid vaporizer system may be utilized in connection with and benefit from the various aspects of the present invention. The exemplary description provided herein is not intended to be limiting in any way, but rather is provided simply to illustrate various aspects of one embodiment of the present invention.

Figure 4:
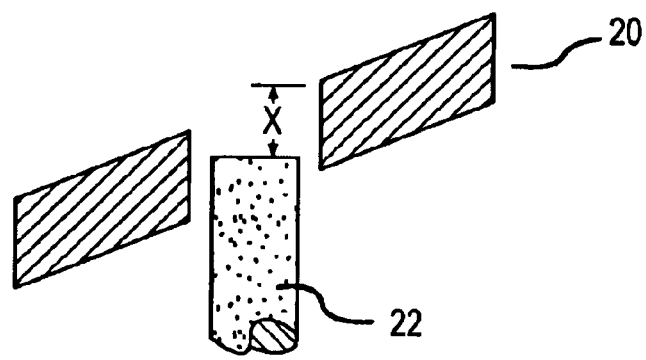
FIG. 4 is a cross-sectional close-up view of an exemplary liquid vaporizer system in accordance with various aspects of the present invention, used in connection with a heating element similar to that of the '053 patent.

With continued reference to FIG. 3 and with additional reference to FIG. 4, exemplary devices suitable for incorporating the present invention include vaporizing devices such as liquid electric air fresheners like those described in U.S. Pat. No. 6,104,867 issued Aug. 15, 2000 to Stathakis et al; U.S. Pat. No. 5,647,053 issued Jul. 8, 1997 to Schroeder et al; and U.S. Pat. No. 5,038,394 issued Aug. 6, 1991 to Hasegawa et al. although, generally speaking, various aspects of the present invention can be incorporated in any number of devices, now known or as yet unknown in the art, designed for transporting fluid through a wick or other similar mechanism, and air freshening devices are merely non-limiting examples.

Housing unit 12 generally includes some type of a vent system 16 and an electrical plug unit 18. Housing unit 12 also suitably includes a heating element 20. Typically, such heating units comprise a heating element which can be readily and reliably charged through use in a conventional outlet. In this manner, heating element 20 is electrically connected to plug unit 18 (not shown).

Liquid reservoir 14 suitably comprises some form of a bottle or other liquid containment material. Reservoir 14 is suitably configured for receipt of a vaporizable liquid device. Such liquid material is suitably presented for vaporization through a wick 22. In accordance with various aspects of the present invention, the vaporizable material can be any number of conventional materials dispensed from vapor dispensers including fragrances, disinfectants, sanitizing agents, insect repellents, insecticides and the like. Preferably, in accordance with a preferred aspect of the present invention, the material to be volatized comprises a fragrance material and system 10 is suitably configured for use as an air-freshening device. In this manner, reservoir 14 is suitably filled with a fragrance containing material inserted into housing unit 12 such that the fragrance material can be vaporized through operation of heater unit 20. Inasmuch as the operation of liquid vaporizers of this type is generally known to those of skill in the art, the operation will not be described in detail herein. Suffice it to say, however, that in accordance with various aspects of a preferred embodiment of the present invention, the vapor dispensing system 10 suitably includes some form of housing 12, reservoir 14, and heating element 20 such that when electrical plug unit 18 is plugged into a conventional electrical outlet heater unit is activated.

Figure 1A:
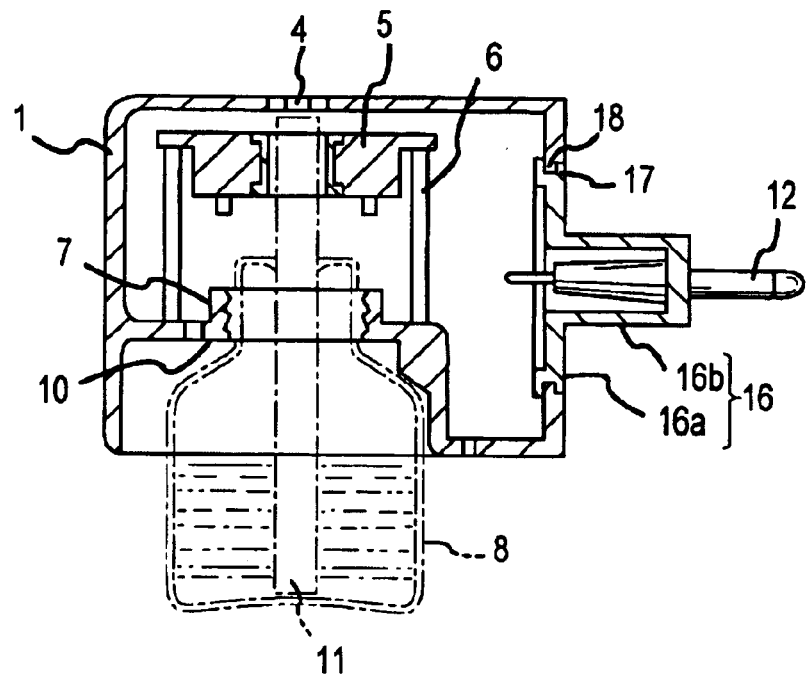
FIGS. 1A and 1B are cross-sectional views of the thermal vaporizer disclosed in U.S. Pat. No. 5,038,394 issued Aug. 6, 1991 to Hasegawa et al. wherein FIG. 1A corresponds to FIG. 5 of the '394 patent and FIG. 1B corresponds to FIG. 10 of the '394 patent.
Figure 1B:
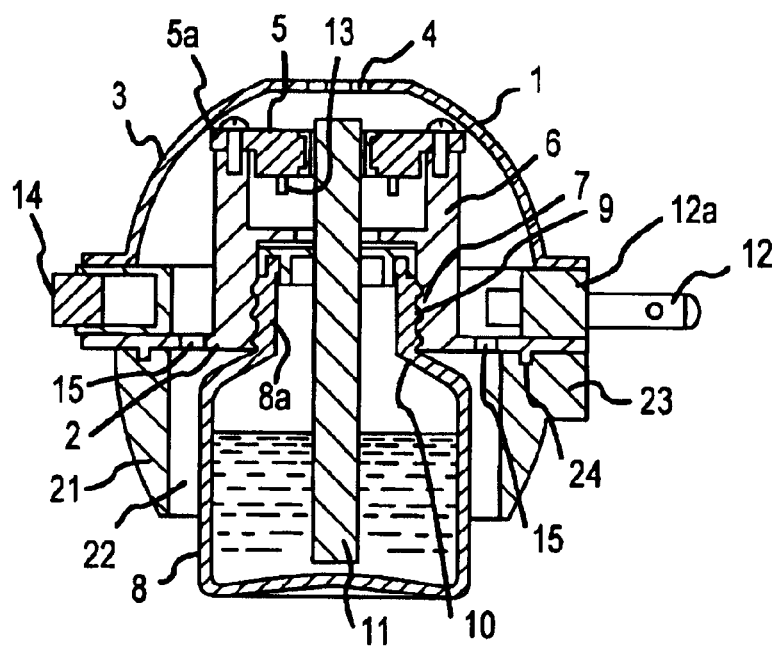
Figure 2A:
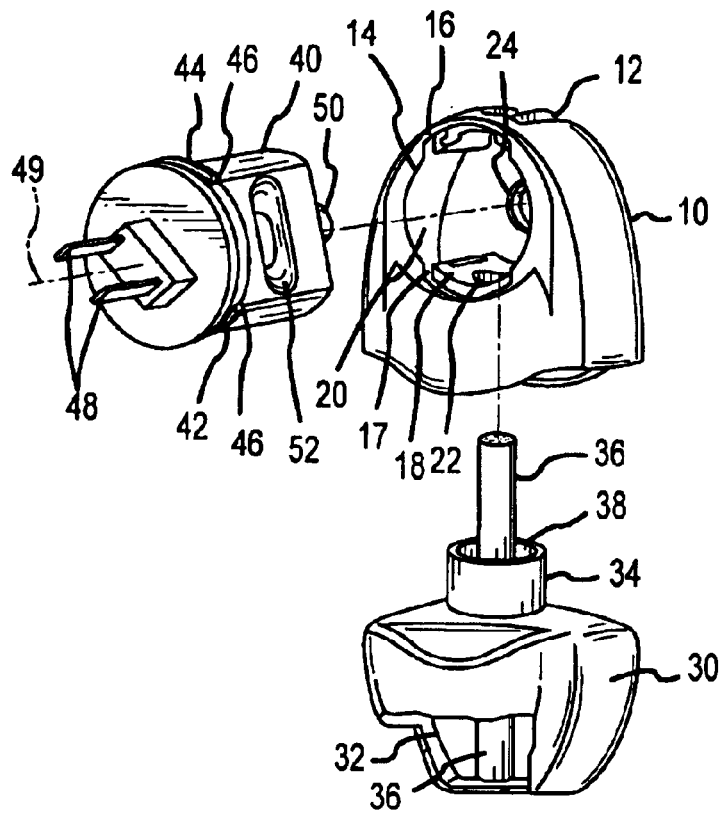
FIGS. 2A and 2B illustrate the vapor dispensing device described in U.S. Pat. No. 5,647,053 issued Jul. 8, 1997 to Schroeder et al., wherein FIG. 2A corresponds to FIG. 1 of the '053 patent and FIG. 2B corresponds to FIG. 4 of the '053 patent.
Figure 2B:
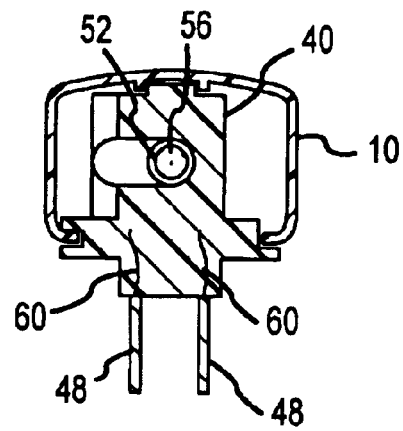

As discussed in greater detail hereinabove, prior art systems require that the wick pass through a wick opening formed in the heating element. For example, as described in U.S. Pat. No. 5,038,394, issued Aug. 6, 1991, to Hasegawa, et al., the wick material of the refill bottle is inserted into the ring heater concentrically therewith. As described in the Hasegawa '394 patent, in such a state, the heater is energized and the upper portion of the wick is heated to thereby cause vaporization of the liquid material to be vaporized. See, for example, FIGS. 1A and 1B. Similarly, as described in U.S. Pat. No. 5,647,053, issued Jul. 8, 1997 to Schroeder, et al., typically the top of the wick will extend to above the top of the heating unit so as to enable the heat generated by the heating element to be near the top of the wick. Additionally, the heating element 52 of devices such as those disclosed by the '053 patent are configured with an angled, annular shape. See, for example, FIGS. 2A and 2B. Thus, various sides of the wick are heated in different areas.

In contradistinction to the arrangements shown in the prior art, the present inventors have found that effective fluid delivery can be obtained while avoiding the disadvantages of the prior art by suitably selecting appropriate wick materials and locating the wick structure, for example wick 22, within an effective heating zone, which zone, while proximate the heating element, for example heating unit 20, does not require wick 22 to pass well into or all the way through heating unit 20.

In accordance with various aspects of the present invention, the wick material is suitably selected to serve as an effective fluid transport mechanism. Exemplary wick materials include any material which may be suitably configured to exhibit acceptable porosity, and thus, acceptable transport kinetics. Stated another way, in accordance with various aspects of the present invention, suitable wick materials include those with effective wicking properties. Moreover, other wick materials which permit relatively rapid transport kinetics also may suitably be utilized. For example, various graphite, ceramic, polymeric, or fibrous wicks may be utilized.

Nonetheless, notwithstanding this preference, in each case, it is desirable that the wick material effectively transport the liquid to be vaporized in a substantially uniform manner. It is also preferable that the wick materials be used in an unsheathed fashion. However, in certain applications sheaths may be used; for example, in cases where effective delivery of the volatile material to be vaporized is transported by the wick material to the uppermost portion of the wick. For example, in certain instances where wicks of significant diameters are used, sufficient liquid to be vaporized (e.g., fragrance) may be delivered to the uppermost portion of the wick and in such case sheaths may be adequately employed.

Surprisingly, the present inventors have found that contrary to the teachings of the prior art, there is an effective range within which the wick may be placed and effective vaporization occurs. In this regard, "vaporization," as used herein is used not only in a conventional sense, but also to include the formation of small aerosol-sized particles. That is, vaporization refers not only to the actual vapors but also to these small particles which can remain suspended for extended periods of time. Such vapors are generally caused to be evacuated from the device, such as through vent 16.

That being said, in accordance with various aspects of the present invention, suitable wick materials are selected and placed within an effective region surrounding heating element, such as heating element 20. This effective region may be defined in many ways and in part depends upon the particular temperature of the heating element. While certain limitations on the temperatures exist, particularly for air freshening devices, in general, those devices which operate at higher temperatures include larger regions within which vaporization continues to be effective. In accordance with various aspects of the present invention, the effective region refers to that varying region which, in part, is temperature dependent.

In accordance with various aspects of the present invention, preferably a suitably selected wick material is placed such that the uppermost portion thereof is located at an effective distance X, as shown in FIGS. 3 and 4, from the upper most portion of the heating element, for example, heating element 20. In accordance with various aspects of the present invention, the effective distance X is preferably between about 1.0 to 2.0 cm from the top of the heating element and most preferably, the distance X from the top of the heating element is about 1.5 to 2.0 cm as this results in a preferred weight of fragrance evaporated over a given period of time. For example, Table 1 below illustrates the amount, in grams, of fragrance evaporated for a porous plastic wick, at a given distance from the top of the heating unit (0, 0.75 and 1.5 cm), over a given period of time (7, 14 and 21 days):

TABLE 1

| Wick Position from Top of Heating Element (cm) | 7 days | 14 days | 21 days |
| --- | --- | --- | --- |
| 1.5 | 5.83 (grams of fragrance evaporated) | 10.00 | 13.51 |
| 0.75 | 7.01 | 12.01 | 16.25 |
| 0.0 | 6.61 | 10.87 | 12.29 |

In this case, a wick position of 1.5 cm from the top of the heating element gave an amount of fragrance evaporated which is suitably uniform (in grams per seven days) over a 21 day period, with acceptable fragrance intensity over that period of time.

The inventors also discovered that the present invention had effective fragrance delivery by varying the amount of wick covered by a sheath as required by some known vaporizing devices in conjunction with adjusting the position of the wick relative to the top of the heating element. For example, Table 2 below illustrates the amount, in grams, of fragrance evaporated from a porous plastic wick, at a distance of about 1.5 cm from the top of the heating unit, with varying amounts of exposed wick (simulating the amount of the wick covered by a sheath) over given periods of time:

TABLE 2

| Amount of Exposed Wick | 7 days | 15 days | 22 days | 29 days | 36 days | 43 days | 50 days | 62 days |
| --- | --- | --- | --- | --- | --- | --- | --- | --- |
| 0.0 cm (sheathed to top of wick) | 2.13 | 4.51 | 6.72 | 8.82 | 10.94 | 13.01 | 14.73 | 17.79 |
| 0.5 | 3.79 | 6.96 | 10.05 | 13.48 | 16.86 | 19.88 | 20.29 | 20.48 |
| 1.0 | 5.24 | 9.73 | 13.07 | 16.19 | 19.24 | 20.09 | 20.24 | 20.32 |
| 1.5 | 5.64 | 10.62 | 14.43 | 18.11 | 20.11 | 20.35 | 20.42 | 20.49 |

TABLE 2-continued

| Amount of Exposed Wick | 7 days | 15 days | 22 days | 29 days | 36 days | 43 days | 50 days | 62 days |
|---|---|---|---|---|---|---|---|---|
| 2.0 | 6.32 | 11.10 | 14.97 | 16.16 | 20.09 | 20.26 | 20.33 | 20.37 |
| 2.5 (no sheath) | 8.23 | 10.26 | 13.58 | 16.94 | 20.08 | 20.41 | 20.49 | 20.53 |

Porous plastic wicks were substituted for the experiments of Table 2, all other factors being the same, and again, effective fragrance delivery was found. That is, in this case, a wick position of 1.5 cm from the top of the heating element gave an amount of fragrance evaporated which is suitably uniform (in grams dispensed per seven days) over a 62 day period, with acceptable fragrance intensity over that period of time.

The inventors also discovered that the present invention had effective fragrance delivery using wick materials other than porous plastics, also with varying amounts of a sheath by adjusting the position of the wick relative to the top of the heating element. For example, Table 3 illustrates the amount, in grams, of fragrance evaporated from a graphite wick, at a distance of about 1.5 cm from the top of the heating unit, with varying amounts of exposed wick (simulating the amount of the wick covered by a sheath) over given periods of time:

TABLE 3

| Amount of Exposed Wick | 7 days | 15 days | 22 days | 29 days | 36 days | 43 days | 50 days | 62 days |
|---|---|---|---|---|---|---|---|---|
| 0.0 cm (sheathed to top of wick) | 1.68 | 3.28 | 4.57 | 5.84 | 6.98 | 8.02 | 8.96 | 10.45 |
| 0.5 | 2.62 | 4.88 | 6.68 | 8.45 | 10.19 | 11.77 | 13.07 | 15.33 |
| 1.0 | 3.90 | 7.22 | 9.77 | 11.84 | 13.83 | 15.72 | 17.29 | 19.38 |
| 1.5 | 4.51 | 8.01 | 10.50 | 12.98 | 15.33 | 17.50 | 19.38 | 19.59 |
| 2.0 | 5.64 | 9.63 | 12.78 | 15.79 | 18.88 | 19.77 | 19.94 | 20.06 |
| 2.5 (no sheath) | 3.89 | 7.23 | 9.53 | 11.70 | 13.94 | 15.96 | 17.82 | 20.68 |

Thus, selection of an effective heating zone, below the uppermost portion of the wick, and optionally, selecting varying amounts of sheath coverings, results in improved fragrance intensity delivery and control. Again, a wick position of 1.5 cm from the top of the heating element gave an amount of fragrance evaporated which is suitably uniform (in grams per seven days) over a 62 day period, while having acceptable fragrance intensity over that period of time.

In accordance with a further embodiment of the present invention, the wick materials selected may be suitably configured to enhance exposed wick surface area thereby tending to enhance evaporation and, accordingly, vaporization while maintaining minimal wick height. For example, the wick may exhibit any number of sizes, dimensions, and/or combinations thereof which enhance exposed surface area. For example, conically-shaped wicks may be utilized, in addition, suitable wick fitment devices may be selected so as to further enhance exposed wick surface area.

Thus, through selection of an effective heating zone and/or through the use of varying sheaths on wicks, advantages over the prior art are realized. For example, among others, wicks are less susceptible to damage through contact with the heating element, the amount of materials are minimized, thus reducing cost, and fragrance intensity and uniformity are improved.

Lastly, it is noted that various principles of the invention have been described in illustrative embodiments. However, many combinations and modifications of the above-described structures, arrangements, proportions, elements, materials and components, used in the practice of the invention, in addition to those not specifically described, may be varied and particularly adapted to specific environments and operating requirements without departing from those principles.

What is claimed is:

1. In a liquid vaporizer of the type comprising a fluid reservoir containing a liquid to be vaporized and an angled, circumferentially oriented heating element, the liquid which is transported from the fluid reservoir by an exposed wick material, improved wherein, the wick material is selectively positioned proximate to, but not extending completely through the angled, circumferentially oriented heating element.

2. The improved vaporizer of claim 1, wherein said effective operation zone is determined by the distance between the upper most portion of the heating element and the uppermost portion of the wick material, and wherein said distance is in the order of about 1.0 cm to about 2.0 cm.

3. The improved vaporizer of claim 2, wherein said distance is about 1.5 cm to about 2.0 cm.

4. The improved vaporizer of claim 3, wherein the temperature in said effective operation zone is higher than the temperature outside of said effective operation zone.

5. The improved vaporizer of claim 1, wherein the wick material does not have a sheath.

6. The improved vaporizer of claim 1, wherein the wick material is a porous plastic material.

7. The improved vaporizer of claim 1, wherein the wick material is a graphite material.

8. The improved vaporizer of claim 1, wherein the liquid is vaporized at a substantially uniform rate from about 0.5 g to about 7 g per week.

9. The improved vaporizer of claim 8, wherein the liquid is vaporized at a substantially uniform rate from about 5 g.

* * * * *